United States Patent
Eilers

(10) Patent No.: US 11,684,702 B2
(45) Date of Patent: Jun. 27, 2023

(54) GAP CONTROL IN ELECTROSURGICAL INSTRUMENTS USING EXPANDED POLYTETRAFLUOROETHYLENE

(71) Applicant: Conmed Corporation, Utica, NY (US)

(72) Inventor: Derek Eilers, Denver, CO (US)

(73) Assignee: Conmed Corporation, Utica, NY (US)

( * ) Notice: Subject to any disclaimer, the term of this patent is extended or adjusted under 35 U.S.C. 154(b) by 413 days.

(21) Appl. No.: 15/930,610

(22) Filed: May 13, 2020

(65) Prior Publication Data

US 2020/0368401 A1 Nov. 26, 2020

Related U.S. Application Data

(60) Provisional application No. 62/852,325, filed on May 24, 2019.

(51) Int. Cl.
| | |
|---|---|
| A61L 31/10 | (2006.01) |
| A61B 18/14 | (2006.01) |
| A61L 31/14 | (2006.01) |
| A61L 31/04 | (2006.01) |
| A61B 18/00 | (2006.01) |

(52) U.S. Cl.
CPC .......... *A61L 31/10* (2013.01); *A61B 18/1445* (2013.01); *A61L 31/048* (2013.01); *A61L 31/146* (2013.01); *A61B 2018/0013* (2013.01); *A61B 2018/0063* (2013.01); *A61B 2018/00083* (2013.01); *A61B 2018/00136* (2013.01); *A61B 2018/00345* (2013.01); *A61B 2018/1467* (2013.01)

(58) Field of Classification Search
CPC .......................... A61L 31/10; A61B 18/1445
USPC ........................................................ 606/51
See application file for complete search history.

(56) References Cited

U.S. PATENT DOCUMENTS

| | | | | |
|---|---|---|---|---|
| 3,970,088 | A * | 7/1976 | Morrison | A61B 18/1402 606/50 |
| 4,607,644 | A * | 8/1986 | Pohndorf | A61N 1/0587 600/391 |
| 4,865,925 | A * | 9/1989 | Ludwig | H01M 4/926 429/480 |
| 4,972,846 | A * | 11/1990 | Owens | A61N 1/0587 607/129 |
| 5,090,422 | A * | 2/1992 | Dahl | A61N 1/056 600/375 |
| 5,269,810 | A * | 12/1993 | Hull | A61N 1/04 607/129 |
| 5,358,516 | A * | 10/1994 | Myers | H01B 7/2825 607/116 |
| 5,466,252 | A * | 11/1995 | Soukup | A61N 1/05 607/116 |
| 5,609,622 | A * | 3/1997 | Soukup | A61N 1/056 607/122 |

(Continued)

*Primary Examiner* — Carl H Layno
*Assistant Examiner* — Manolis Pahakis
(74) *Attorney, Agent, or Firm* — Bond, Schoeneck & King, PLLC

(57) ABSTRACT

An electrosurgical device having a pair of jaws, at least one electrode supported by one of the pair of jaws, and a sheet of expanded polytetrafluoroethylene positioned in covering relation to at least a portion of the at least one electrode. The sheet may have a porosity of between thirty and ninety percent. The sheet may have a plurality of pores with an average diameter of between 0.2 and 1.0 micrometers.

10 Claims, 5 Drawing Sheets

(56) References Cited

U.S. PATENT DOCUMENTS

| | | | | |
|---|---|---|---|---|
| 5,755,762 A * | 5/1998 | Bush | A61N 1/056 | 607/121 |
| 5,931,862 A * | 8/1999 | Carson | A61N 1/0563 | 607/116 |
| 6,227,203 B1 * | 5/2001 | Rise | A61M 5/14276 | 607/46 |
| 6,546,292 B1 * | 4/2003 | Steinhaus | A61N 1/0565 | 607/121 |
| 7,780,663 B2 * | 8/2010 | Yates | A61B 17/07207 | 606/151 |
| 8,790,342 B2 * | 7/2014 | Stulen | A61B 18/1445 | 606/45 |
| 8,795,276 B2 * | 8/2014 | Dietz | A61B 18/1445 | 606/41 |
| 8,888,776 B2 * | 11/2014 | Dietz | A61B 18/1445 | 606/51 |
| 8,926,607 B2 * | 1/2015 | Norvell | A61B 18/1445 | 606/41 |
| 2002/0147486 A1 * | 10/2002 | Soukup | A61N 1/0563 | 607/36 |
| 2003/0023294 A1 * | 1/2003 | Krall | A61N 1/0563 | 607/122 |
| 2003/0073991 A1 * | 4/2003 | Francischelli | A61B 18/1442 | 606/41 |
| 2003/0105506 A1 * | 6/2003 | Krishnan | A61N 1/056 | 607/126 |
| 2003/0212394 A1 * | 11/2003 | Pearson | A61B 18/1477 | 606/41 |
| 2004/0147922 A1 * | 7/2004 | Keppel | A61B 18/14 | 606/41 |
| 2004/0176672 A1 * | 9/2004 | Silver | A61B 5/14865 | 600/364 |
| 2004/0230275 A1 * | 11/2004 | Marshall | A61N 1/0568 | 607/122 |
| 2004/0230276 A1 * | 11/2004 | Marshall | A61N 1/0568 | 607/122 |
| 2004/0230281 A1 * | 11/2004 | Heil | A61N 1/36585 | 607/126 |
| 2005/0015082 A1 * | 1/2005 | O'Sullivan | A61B 5/287 | 606/41 |
| 2005/0080470 A1 * | 4/2005 | Westlund | A61N 1/0587 | 607/119 |
| 2005/0131511 A1 * | 6/2005 | Westlund | A61N 1/0587 | 607/126 |
| 2006/0079740 A1 * | 4/2006 | Silver | A61B 5/6882 | 600/353 |
| 2006/0195079 A1 * | 8/2006 | Eberl | A61B 18/1492 | 606/49 |
| 2006/0257995 A1 * | 11/2006 | Simpson | A61B 5/14532 | 435/287.2 |
| 2007/0134407 A1 * | 6/2007 | Yang | H01M 4/8828 | 502/101 |
| 2008/0077131 A1 * | 3/2008 | Yates | A61B 17/07207 | 606/51 |
| 2008/0077220 A1 * | 3/2008 | Reddy | A61N 1/057 | 607/131 |
| 2008/0183261 A1 * | 7/2008 | Hammill | A61N 1/0563 | 607/119 |
| 2009/0223701 A1 * | 9/2009 | Idomoto | H05K 3/0014 | 428/137 |
| 2011/0087337 A1 * | 4/2011 | Forsell | A61B 17/12 | 600/38 |
| 2011/0208067 A1 * | 8/2011 | Edman | A61B 5/02007 | 600/486 |
| 2011/0306963 A1 * | 12/2011 | Dietz | A61B 18/1445 | 606/41 |
| 2011/0306964 A1 * | 12/2011 | Stulen | A61B 18/1445 | 606/41 |
| 2011/0306965 A1 * | 12/2011 | Norvell | A61B 18/1445 | 606/41 |
| 2011/0306966 A1 * | 12/2011 | Dietz | A61B 18/1445 | 606/41 |
| 2016/0128694 A1 * | 5/2016 | Baxter, III | A61B 17/105 | 227/176.1 |
| 2016/0164120 A1 * | 6/2016 | Swiegers | C25C 7/00 | 429/446 |
| 2017/0325724 A1 * | 11/2017 | Wang | A61B 5/1486 | |
| 2018/0249767 A1 * | 9/2018 | Begriche | A61B 5/25 | |
| 2018/0269491 A1 * | 9/2018 | Cho | H01M 8/1018 | |
| 2018/0375106 A1 * | 12/2018 | Tanimura | H01M 8/10 | |
| 2020/0083541 A1 * | 3/2020 | Swiegers | H01M 8/0239 | |
| 2020/0212467 A1 * | 7/2020 | Kim | H01M 8/1044 | |
| 2020/0368401 A1 * | 11/2020 | Eilers, Jr. | A61L 31/10 | |

\* cited by examiner

GAP CONTROL IN ELECTROSURGICAL INSTRUMENTS USING EXPANDED POLYTETRAFLUOROETHYLENE

CROSS-REFERENCE TO RELATED APPLICATIONS

The present application claims priority to U.S. Provisional No. 62/852,325, filed on May 24, 2019.

BACKGROUND OF THE INVENTION

1. Field of the Invention

The present invention relates to electrosurgical instruments and, more specifically, to an expanded polytetrafluoroethylene coating for controlling the distance between the electrodes of the jaws of a bipolar electrosurgical vessel sealer.

2. Description of the Related Art

Electrosurgical vessel sealers have become a commonly used tool for surgical procedures. A vessel sealer works by delivering electromagnetic energy to one or more electrodes that are carried by a pair of opposing jaws to perform cutting and/or coagulation of tissue to be treated. For safe and effective operation, the electrodes of the vessel sealer must remain separated by approximately 0.002 to 0.006 inches (0.0508 to 0.1524 millimeters) when clamping a blood vessel to prevent arcing or shorting when the electrodes are energized. As the blood vessel does not typically occupy the entire region between the electrodes, there is a constant risk that the electrodes will be allowed to come into contact with each other or become so closely positioned that arcing or shorting will occur. Current approaches for maintaining the appropriate electrode separate involve non-conducting blocks or stops that are positioned along the electrodes to physically prevent the electrodes from becoming too closely positioned relative to each other when energized. While stops can maintain the proper distance between the electrodes, they are difficult to install and thus increase the costs and complexity involved in the manufacturing of the vessel sealer. Accordingly, there is a need in the art for an approach that can ensure the appropriate gap between the electrodes of the vessel sealer without the need to form or place physical stops along the jaws.

BRIEF SUMMARY OF THE INVENTION

The present invention comprises an approach for creating a gap between the electrodes of an electrosurgical device to prevent shorting. More specifically, the present invention comprises an electrosurgical device having a pair of jaws, at least one electrode supported by one of the pair of jaws, and a sheet of expanded polytetrafluoroethylene positioned in covering relation to at least a portion of the at least one electrode. The sheet may have a porosity of between thirty and ninety percent. The sheet may have a plurality of pores with an average diameter of between 0.2 and 1.0 micrometers.

The present invention also comprises a method of protecting an electrosurgical device. A first step comprises providing an electrosurgical device having a pair of jaws and at least one electrode supported by one of the pair of jaws. A next step comprises positioning a sheet of expanded polytetrafluoroethylene in covering relation to a portion of the at least one electrode. The sheet may have a porosity of between thirty and ninety percent. The sheet may have a plurality of pores with an average diameter of between 0.2 and 1.0 micrometers. The step of positioning a sheet of expanded polytetrafluoroethylene in covering relation to a portion of the at least one electrode may comprise the step of adhering the sheet to the at least one electrode using an adhesive. The step of positioning a sheet of expanded polytetrafluoroethylene in covering relation to a portion of the at least one electrode may comprise the step of forming an overmold over a portion of the sheet.

The present invention may further comprise a method of operating an electrosurgical device. A first step may comprise providing an electrosurgical device having a pair of jaws, at least one electrode supported by one of the pair of jaws, and a sheet of expanded polytetrafluoroethylene in covering relation to a portion of the at least one electrode. A next step may comprise closing the electrosurgical device about a portion of tissue to be treated. A further step may comprise energizing the electrosurgical device to accomplish a surgical procedure without any shorting between the electrodes. The sheet may have a porosity of between thirty and ninety percent. The sheet may have a plurality of pores with an average diameter of between 0.2 and 1.0 micrometers.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 4:
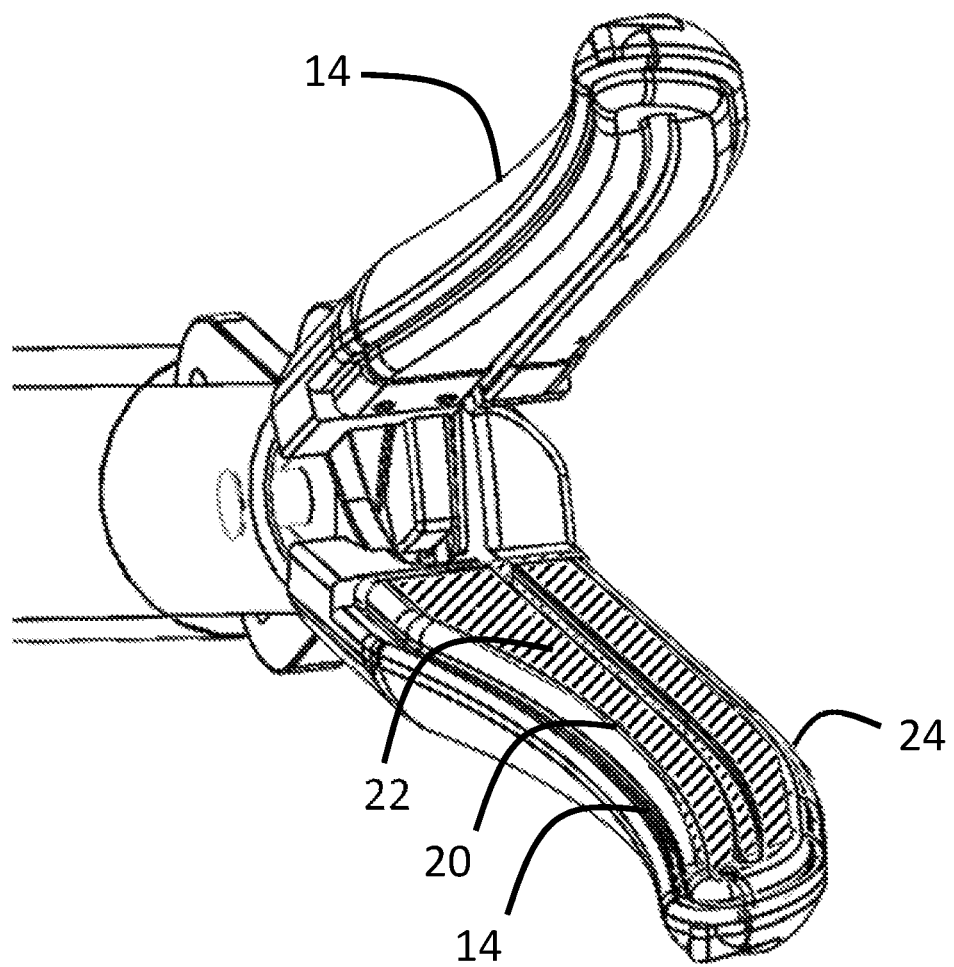
Figure 5:
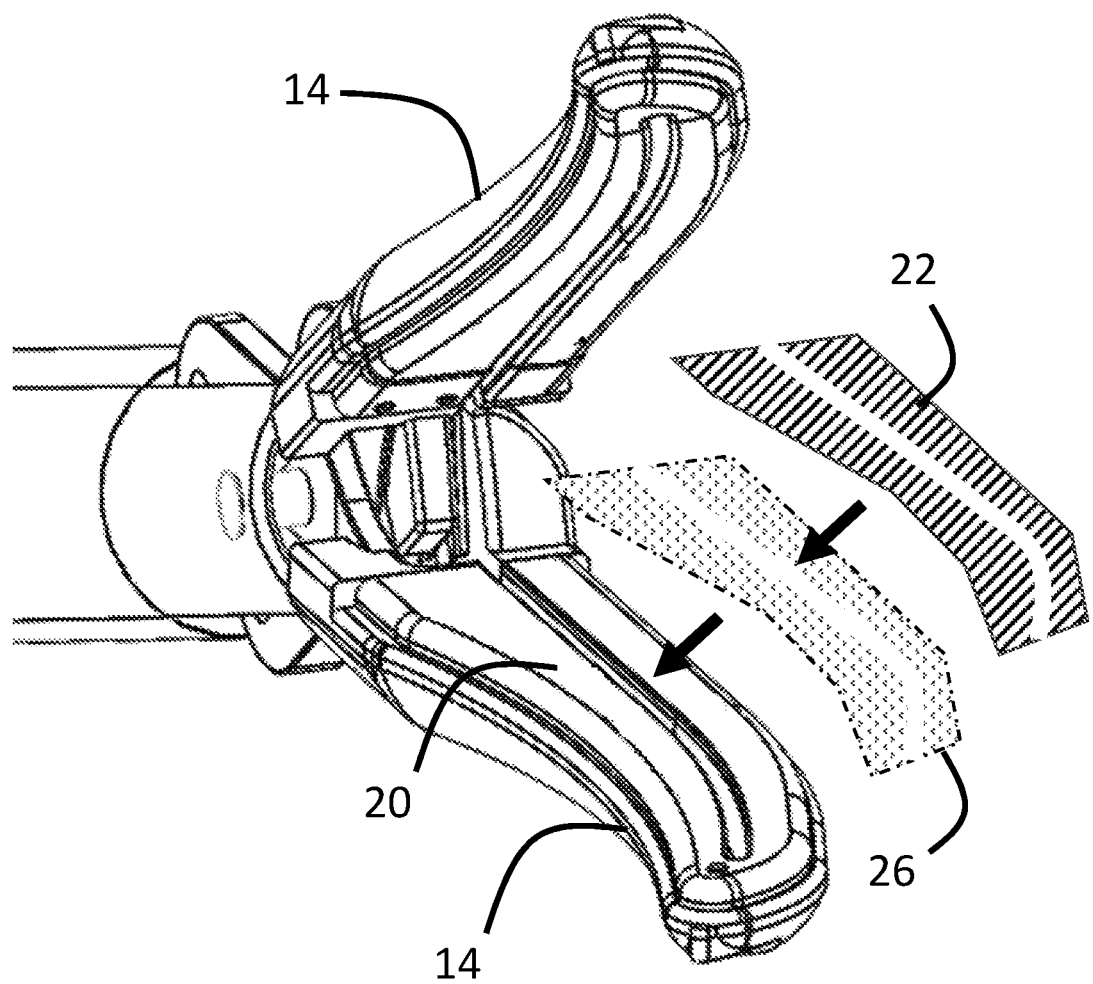

FIG. 4 is a perspective view of a sheet of expanded polytetrafluoroethylene applied to the electrodes of the jaws of an electrosurgical vessel sealer and held thereon by an overmold according to the present invention; and FIG. 5 is a perspective view of a sheet of expanded polytetrafluoroethylene being applied to the electrodes of the jaws of an electrosurgical vessel sealer using an adhesive according to the present invention.

DETAILED DESCRIPTION OF THE INVENTION

Figure 1:
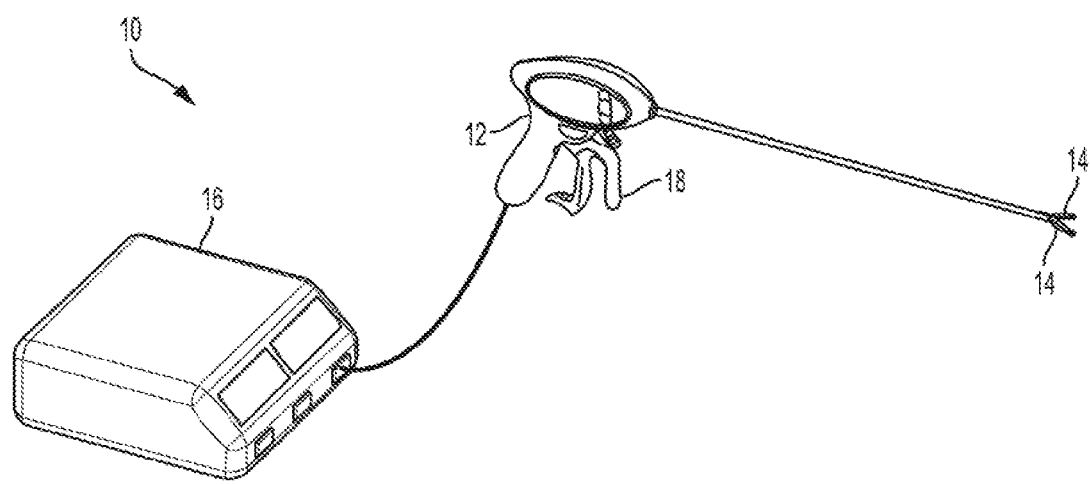
FIG. 1 is a schematic of an electrosurgical system having a pair of jaws carrying electrodes for electrosurgically treating tissue.

Referring to the figures, wherein like numeral refer to like parts throughout, there is seen in FIG. 1 a vessel sealing system 10 comprising a vessel sealer 12 having a pair of conductive opposing jaws 14 that are interconnected to an electrosurgical generator 16 that can supply RF energy to electrodes of jaws 14 for the desiccation of a blood vessel trapped between jaw 14. The dimensions of jaw 14 and the type of RF energy supplied will produce desiccation of the blood vessel in a region of a particular width as determined by the thermal spread of the energy being supplied to the blood vessel. As is known in the art, jaws 14 are pivotally mounted to vessel sealer 12 for movement between an open position and a closed position in response to a user operating a handle 18 of sealer 12.

Figure 2:
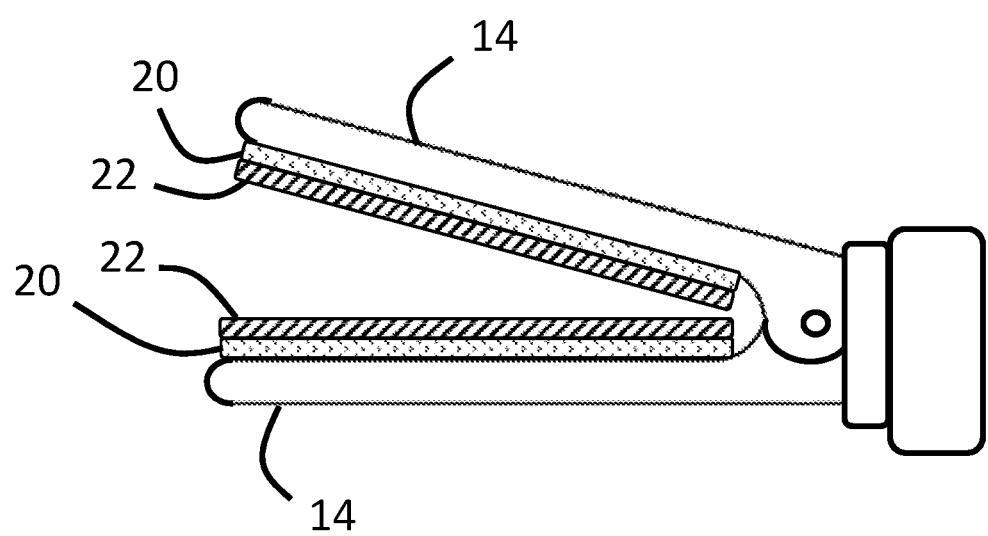
FIG. 2 is a side view of a pair of jaws of an electrosurgical vessel sealer having a sheet of expanded polytetrafluoroethylene applied to the electrodes of the jaws of an electrosurgical vessel sealer according to the present invention.

Referring to FIG. 2, jaws 14 of vessel sealer 12 carry a pair of corresponding electrodes 20. Each electrode 20 is covered, at least in part, by a sheet 22 of expanded polytetrafluoroethylene (ePTFE). Sheet 22 can be applied to one or both inner facing surfaces of electrodes 20 of vessel sealer 12. Sheet 22 could be of varying thickness (0.002 inches to 0.008 inches) and of varying porosity. While the formation of pores having a controlled size is difficult using conventional PTFE, and thus not readily applicable for use with electrodes 20, ePTFE can provide sufficient control over porosity because the physical stretching of the ePTFE sheet is easier to control using uniaxial or biaxial stretching.

Preferably, sheet 22 is formed from ePTFE having a microporous structure. The preparation of sheet 22 by stretching of PTFE to form ePTFE may be thus be adjusted to achieve the desire result by the modification of three parameters, all of which contribute to the characteristics of final product. First, the temperature must be set appropriately to ensure the material is heated, but not over-heated. Over-heating would mean that the PTFE becomes sintered, which is not desired, so that temperature must be just high enough to ensure that the ePTFE stays soft. The rate at which the PTFE is stretched will define the density of the final product, with lower densities require a higher stretch rate. For example, sheet 22 comprised of ePTFE having a weight of between 1.5 and 40 grams per square meter and a thickness of between 0.00015 and 0.0040 inches may have a pore size between 0.2 and 1.0 micrometers. The porosity of sheet 22 may also be expressed as a function of density, with densities of 1 to 1.5 grams per cubic centimeter having a porosity range of 30 to 50 percent, densities between 0.65 and 1 grams per cubic centimeter having a porosity range of 50 to 70 percent, and densities of between 0.2 and 0.65 having a porosity of between 70 and 90 percent.

Figure 3:
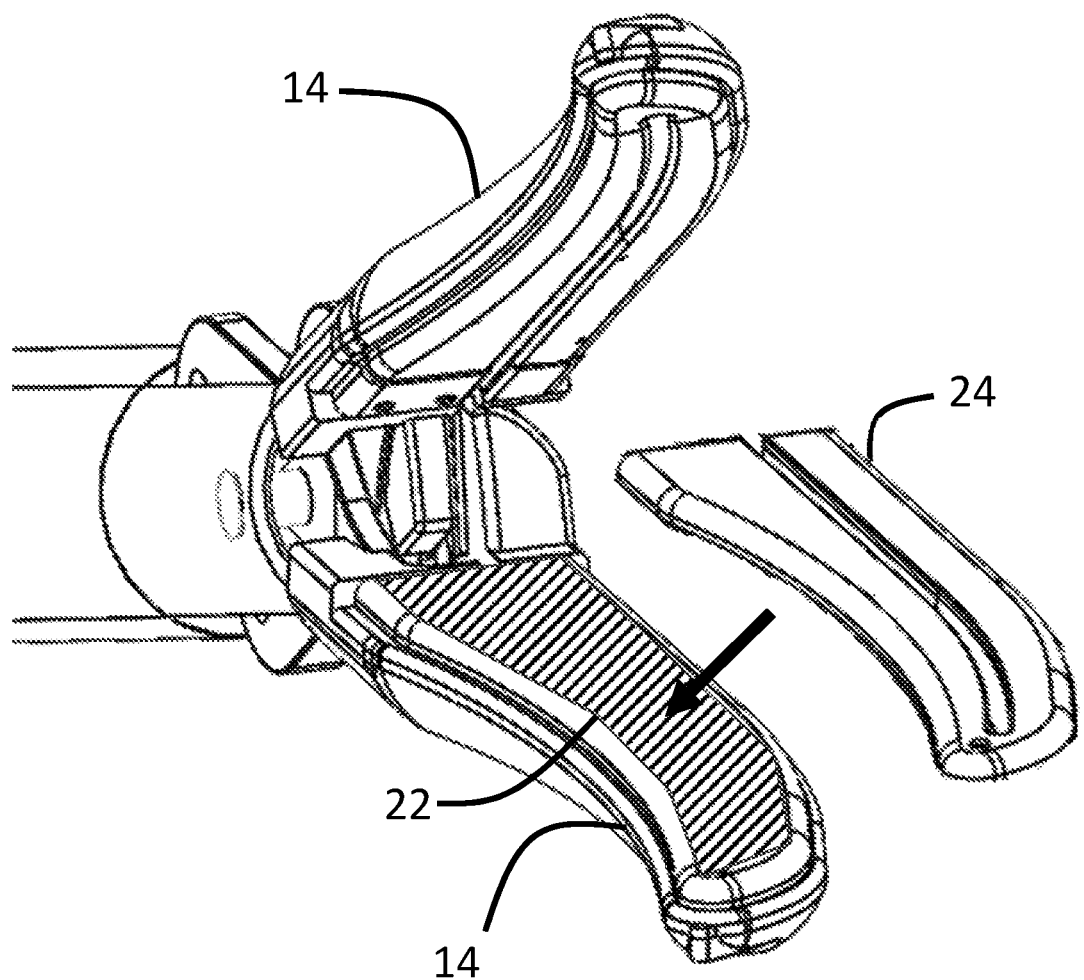
FIG. 3 is a perspective view of an overmold process for applying a sheet of expanded polytetrafluoroethylene to the electrodes of the jaws of an electrosurgical vessel sealer according to the present invention.

Sheet 22 can be affixed to electrode 20 in a variety of ways. For example, as seen in FIGS. 3 and 4, sheet 22 may be mechanically clamped in place by placing sheet 22 in covering relation to electrode 20 and then overmolding to form an overmold 24 over sheet 22 and electrode 20 so that sheet 22 is held in place on electrode 20 by overmold 24 that only extends around the periphery of jaws 14 so that the surface of sheet 22 is exposed over at least a portion of the surface of electrode 20. Alternatively, as seen in FIG. 5, sheet 22 may be cut to size and adhered to each electrode using an adhesive 26.

When jaws 14 are closed, electrodes 20 will be spaced apart from each other by any sheets 22 positioned over either electrode 20. The use of expanded PTFE for sheet 22 will allow for sufficient electrical conductivity when tissue is positioned between jaws 14 and energy is applied by electrosurgical generator 16. As ePTFE is primarily non-conductive, however, sheet 22 will not provide enough conductivity that direct contact between jaws 14 will cause electrodes 20 to form a short condition. As an additional benefit, ePTFE can also prevent sticking of tissue during the application of energy.

What is claimed is:

1. An electrosurgical device, comprising:
   a pair of jaws;
   at least one electrode supported by one of the pair of jaws; and
   a sheet of expanded polytetrafluoroethylene positioned in covering relation to at least a portion of the at least one electrode, wherein the sheet has a porosity of between thirty and ninety percent.

2. The electrosurgical device of claim 1, wherein the sheet has a plurality of pores with an average diameter of between 0.2 and 1.0 micrometers.

3. A method of protecting an electrosurgical device, comprising the steps of:
   providing an electrosurgical device having a pair of jaws and at least one electrode supported by one of the pair of jaws; and
   positioning a sheet of expanded polytetrafluoroethylene in covering relation to a portion of the at least one electrode, wherein the sheet has a porosity of between thirty and ninety percent.

4. The method of claim 3, wherein the sheet has a porosity of between thirty and ninety percent.

5. The method of claim 4, wherein the sheet has a plurality of pores with an average diameter of between 0.2 and 1.0 micrometers.

6. The method of claim 3, wherein the step of positioning a sheet of expanded polytetrafluoroethylene in covering relation to a portion of the at least one electrode comprises the step of adhering the sheet to the at least one electrode using an adhesive.

7. The method of claim 3, wherein the step of positioning a sheet of expanded polytetrafluoroethylene in covering relation to a portion of the at least one electrode comprises the step of forming an overmold over a portion of the sheet.

8. A method of operating an electrosurgical device, comprising the steps of:
   providing an electrosurgical device having a pair of jaws, at least one electrode supported by one of the pair of jaws, and a sheet of expanded polytetrafluoroethylene in covering relation to a portion of the at least one electrode, wherein the sheet has a porosity of between thirty and ninety percent;
   closing the electrosurgical device about a portion of tissue to be treated; and
   energizing the electrosurgical device to accomplish a surgical procedure without any shorting between the electrodes.

9. The method of claim 8, wherein the sheet has a porosity of between thirty and ninety percent.

10. The method of claim 8, wherein the sheet has a plurality of pores with an average diameter of between 0.2 and 1.0 micrometers.

* * * * *